(12) United States Patent
Moore

(10) Patent No.: US 12,310,848 B2
(45) Date of Patent: May 27, 2025

(54) LEAFLET ATTACHMENT TO PROSTHETIC HEART VALVE

(71) Applicant: St. Jude Medical, Cardiology Division, Inc., St. Paul, MN (US)

(72) Inventor: Brandon Moore, St. Louis Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 212 days.

(21) Appl. No.: 17/678,401

(22) Filed: Feb. 23, 2022

(65) Prior Publication Data

US 2022/0265423 A1 Aug. 25, 2022

Related U.S. Application Data

(60) Provisional application No. 63/152,908, filed on Feb. 24, 2021.

(51) Int. Cl.
*A61F 2/24* (2006.01)

(52) U.S. Cl.
CPC .... *A61F 2/2418* (2013.01); *A61F 2220/0075* (2013.01); *A61F 2230/0019* (2013.01)

(58) Field of Classification Search
CPC .............................. A61F 2/2418; A61F 2/2463
See application file for complete search history.

(56) References Cited

U.S. PATENT DOCUMENTS

| | | | |
|---|---|---|---|
| 3,657,744 A | 4/1972 | Ersek | |
| 4,056,854 A | 11/1977 | Boretos et al. | |
| 4,610,688 A | 9/1986 | Silvestrini et al. | |
| 5,411,552 A | 5/1995 | Andersen et al. | |
| 5,545,214 A | 8/1996 | Stevens | |
| 5,855,601 A | 1/1999 | Bessler et al. | |
| 5,957,949 A | 9/1999 | Leonhardt et al. | |
| 6,458,153 B1 | 10/2002 | Bailey et al. | |
| 6,540,782 B1 | 4/2003 | Snyders | |
| 7,510,575 B2 | 3/2009 | Spenser et al. | |
| 7,585,321 B2 | 9/2009 | Cribier | |
| 7,682,390 B2 | 3/2010 | Seguin | |
| 7,972,378 B2* | 7/2011 | Tabor | A61F 2/013 623/1.24 |
| 9,056,006 B2 | 6/2015 | Edelman et al. | |
| 9,326,856 B2 | 5/2016 | Schraut et al. | |
| 9,717,593 B2* | 8/2017 | Alkhatib | A61F 2/2418 |
| 10,022,211 B2 | 7/2018 | Braido et al. | |
| 10,039,640 B2 | 8/2018 | Grundeman et al. | |
| 10,143,551 B2 | 12/2018 | Braido et al. | |
| 10,299,915 B2 | 5/2019 | Edelman et al. | |
| 10,751,171 B2* | 8/2020 | Li | A61F 2/2415 |
| 11,273,030 B2* | 3/2022 | Li | A61F 2/2418 |
| 2009/0240320 A1 | 9/2009 | Tuval | |

(Continued)

*Primary Examiner* — Brian A Dukert

(74) *Attorney, Agent, or Firm* — SLEMAN & LUND LLP

(57) ABSTRACT

A prosthetic heart valve includes a stent extending from an inflow end to an outflow end. The stent has a commissure attachment feature between the inflow end and the outflow end. The commissure attachment feature has a frame defining an opening. The valve further includes a skirt coupled to the frame of the commissure attachment feature, and at least two leaflets coupled to the skirt. Each leaflet is coupled to the skirt both through the opening of the commissure attachment feature and outside of the commissure attachment feature.

9 Claims, 6 Drawing Sheets

(56) References Cited

U.S. PATENT DOCUMENTS

| | | |
|---|---|---|
| 2015/0320556 A1 | 11/2015 | Levi et al. |
| 2016/0120646 A1 | 5/2016 | Dwork |
| 2017/0258585 A1 | 9/2017 | Marquez et al. |
| 2018/0055632 A1 | 3/2018 | Hill et al. |
| 2018/0078368 A1 | 3/2018 | Vidlund et al. |
| 2019/0201190 A1 | 7/2019 | Dakin et al. |
| 2019/0374337 A1 | 12/2019 | Zamani |
| 2021/0077254 A1 | 3/2021 | Gale et al. |

\* cited by examiner

LEAFLET ATTACHMENT TO PROSTHETIC HEART VALVE

CROSS REFERENCE TO RELATED APPLICATIONS

This application claims the benefit of the filing date of U.S. Provisional Application No. 63/152,908 filed Feb. 24, 2021, the disclosure of which is hereby incorporated by reference herein in its entirety.

FIELD OF THE INVENTION

The present disclosure relates generally to the field of stents, and in particular, to stents for use in transcatheter prosthetic heart valves. More particularly, the present disclosure is directed to improved methods for manufacturing such stents.

BACKGROUND

Prosthetic heart valves, including surgical heart valves and expandable heart valves intended for transcatheter aortic valve replacement ("TAVR") or transcatheter mitral valve replacement ("TMVR"), are well known in the patent literature. (See U.S. Pat. Nos. 3,657,744; 4,056,854; 5,411,552; 5,545,214; 5,855,601; 5,957,948; 6,458,153; 6,540,782; 7,510,575; 7,585,321; 7,682,390; and 9,326,856; and U.S. Patent Pub. No. 2015/0320556.) Surgical or mechanical heart valves may be sutured into a native heart valve annulus of a patient during an open-heart surgical procedure, for example. Expandable heart valves, on the other hand, may be delivered into a patient via a tube-like delivery apparatus such as a catheter, a trocar, a laparoscopic instrument, or the like to avoid a more invasive procedure such as full open chest, open heart surgery. As used herein, reference to an "expandable" heart valve includes those that are self-expending and those that are mechanically expandable via, for example, a balloon. Often the term "collapsible/expandable" heart valve is used herein and unless the text or the context dictate otherwise, this term is meant to include heart valves that may be collapsed to a small cross-section that enables them to be delivered into a patient through a tube-like delivery apparatus in a minimally invasive procedure, and then self-expanded or mechanically expanded to an operable size once in place.

Prosthetic heart valves typically take the form of a one-way valve structure (often referred to herein as a valve assembly) mounted to/within a stent. In general, expandable heart valves include a self-expanding or balloon expandable stent, often made of a metal, such as Nitinol or stainless steel. The one-way valve assembly mounted to/within the stent includes one or more leaflets, and may also include a cuff or skirt. The cuff may be disposed on the stent's interior or luminal surface, its exterior or abluminal surface, and/or on both surfaces. (See U.S. Pat. Nos. 6,458,153; 7,585,321; 8,992,608; 9,241,794; and 9,289,296; and U.S. Patent Pub. No. 2015/0320556.) The cuff ensures that blood does not just flow around the valve leaflets if the valve or valve assembly are not optimally seated in a native valve annulus. A cuff, or a portion of a cuff, disposed on the exterior of the stent can help retard leakage around the outside of the valve (the latter known as paravalvular or "PV" leakage).

Leaflets, cuffs and valve assemblies for prosthetic heart valves may be derived from various natural tissues or synthetic materials. Commercial natural tissues that have been chemically treated or "fixed" are often used. For example, leaflets could be made of bovine pericardium and cuffs could be made of porcine pericardium. (See, e.g., U.S. Pat. No. 5,957,949 at 6:23-33; U.S. Pat. No. 6,458,153 at 8:28-40; U.S. Pat. No. 5,855,601 at 6:21-30; and U.S. Pat. No. 7,585,321 at 13:5- 36.) Other materials that may be used to form valve components include various synthetic polymers including, without limitation, polytetrafluoroethylene (PTFE) or polyester (see U.S. Pat. No. 5,855,601 at 6:29-31; U.S. Pat. Nos. 10,039,640; 10,022,211; 9,056,006; and 10,299,915; and U.S. Patent Pub. Nos. 2018/0055632; 2017/0258585; 2018/0078368; and 2019/0201190), and elastic materials including silicone rubber and polyurethanes. (See U.S. Pat. No. 6,540,782 at 6:2-5.) These materials have been used in the form of continuous sheets, porous felts (U.S. Pat. No. 6,540,782 at 6:17-23) or woven fabrics. (See also U.S. Pat. Nos. 10,039,640; 10,299,915; 10,022,211; and 4,610,688; and U.S. Patent Pub. Nos. 2018/0055632; 2017/0258585; and 2018/0078368; see also Basir et al., "*Flexible mechanoprosthesis made from woven ultra-high-molecular-weight polyethylene fibers; proof of concept in a chronic sheep model*", Interactive CardioVascular and Thoracic Surgery, 25(2017), 942-949; and Yamagishi and Kurosawa, "*Outflow Reconstruction of Tetralogy of Fallot Using a Gore-Tex Valve*", Ann. Thorac Surg., 1993, 56:1414-17.) Valve components and valve assemblies may be attached to a collapsible/expandable stent or frame by sutures or may be molded, glued, or soldered to the stent. (See U.S. Pat. No. 7,585,321 at 13:30-31.)

Leaflet attachment to the stent or frame of a prosthetic heart valve, such as a transcatheter aortic valve replacement (TAVR), can be challenging from a durability standpoint. Stress is imparted to the leaflets by fluid pressure during valve closure and this stress is transferred to the leaflet attachment points. The commissure regions see particularly high stresses and therefore present a challenge for prosthetic valve design.

BRIEF SUMMARY

According to a first aspect of the disclosure, a prosthetic heart valve includes a stent, a skirt and at least two leaflets. The stent may extend from an inflow end to an outflow end. The stent may have a commissure attachment feature between the inflow end and the outflow end. The commissure attachment feature may have a frame defining an opening. The skirt may be coupled to the frame of the commissure attachment feature. The leaflets may be coupled to the skirt both through the opening of the commissure attachment feature and outside of the commissure attachment feature.

BRIEF DESCRIPTION OF THE DRAWINGS

A more complete appreciation of the subject matter of the present disclosure and the various advantages thereof can be realized by reference to the following detailed description in which reference is made to the accompanying drawings in which.

DETAILED DESCRIPTION

Figure 1:
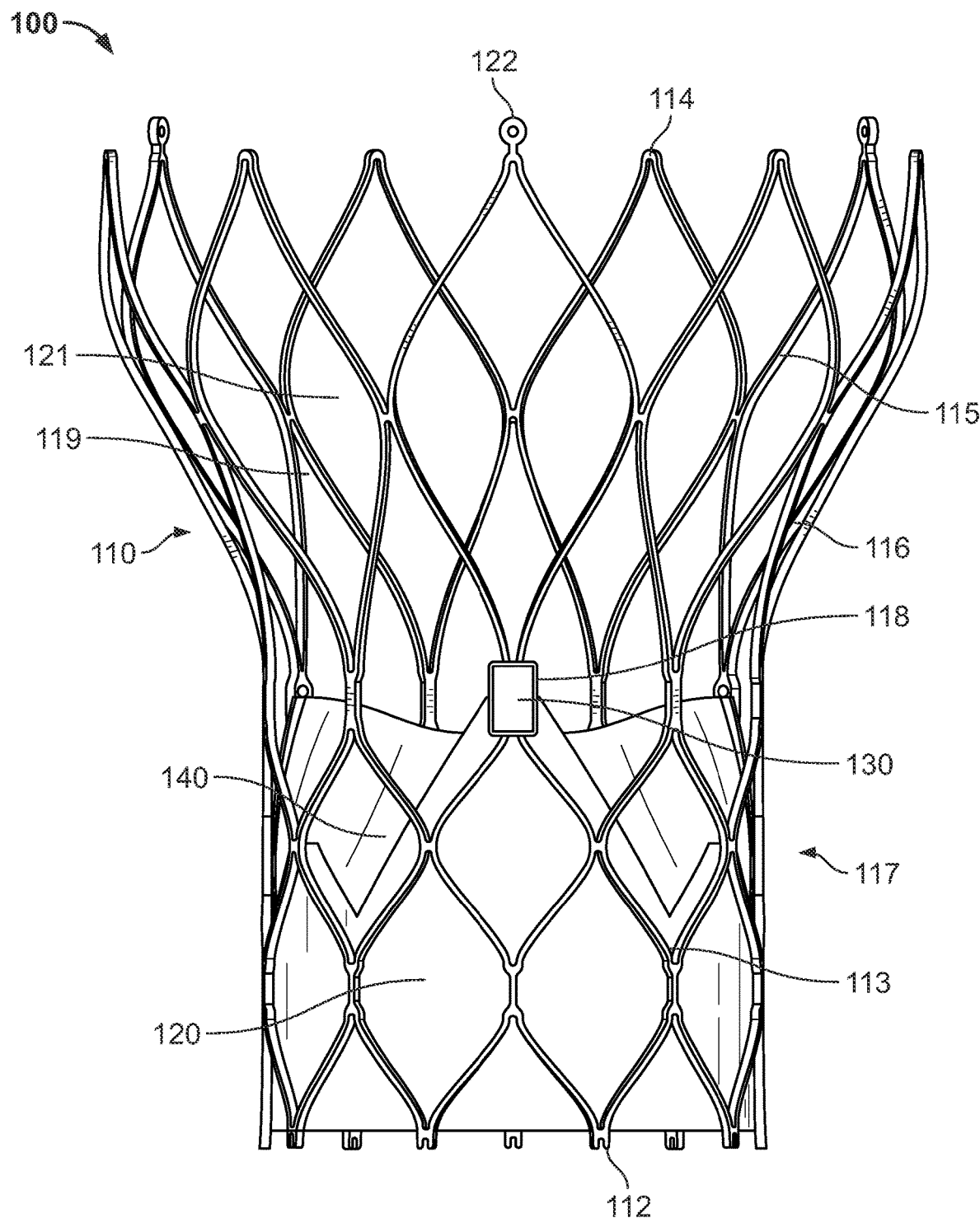
FIG. 1 is a side view of a prosthetic heart valve in accordance with aspects of the disclosure.

As used herein in connection with a prosthetic heart valve, the term "inflow end" refers to the end of the heart valve through which blood enters when the heart valve is functioning as intended, the term "outflow end" refers to the end of the heart valve through which blood exits when the heart valve is functioning as intended, and the term "flow direction" refers to the direction from the inflow end of the heart valve to the outflow end of the heart valve. Thus, for a prosthetic aortic valve properly implanted in a patient, the inflow end is the end nearest the left ventricle, while the outflow end is the end nearest the aorta. As used herein in connection with a prosthetic heart valve, the term "proximal" refers to the inflow end of the heart valve or to elements of the heart valve that are relatively close to the inflow end, and the term "distal" refers to the outflow end of the heart valve or to elements of the heart valve that are relatively close to the outflow end. Also as used herein, the terms "generally," "substantially," "approximately," and "about" are intended to mean that slight deviations from absolute are included within the scope of the term so modified. However, unless otherwise indicated, the lack of any such terms should not be understood to mean than such slight deviations from absolute are not included within the scope of the term so modified.

When used to indicate relative locations within a prosthetic heart valve, the terms "longitudinal" and "vertical" are to be taken as the direction of an axis extending between the inflow end and the outflow end of the prosthetic valve, along the direction of intended blood flow, and the terms "above," "below," "upper," "lower," "high" and "low" are to be taken as relative to the inflow end of the prosthetic valve. "Above," "upper" and "high" are to be understood as relatively farther from the inflow end of the prosthetic valve in the direction of intended blood flow, and "below," "lower" and "low" are to be understood as relatively closer to the inflow end of the prosthetic valve in the direction of intended blood flow. When used to indicate relative locations within the prosthetic heart valve, the terms "radial" or "circumferential" are to be taken as the direction of rotation about the longitudinal axis of the prosthetic valve. As used herein, the prosthetic heart valve, or the stent or frame of the prosthetic heart valve, may assume an "expanded state" and a "collapsed state," which refer to the relative radial size of the stent or heart valve.

Although the various structures and features disclosed herein are described in connection with a prosthetic aortic valve, the same or similar structures and features can be employed in other prosthetic heart valves, such as the pulmonary valve, the mitral valve, and the tricuspid valve, as well as in structures that control the flow of fluid through other lumens or passageways in the body.

A prosthetic heart valve (e.g., an aortic valve) may be implanted into the heart of a patient to replace or improve the operation of the native valve. The prosthetic valve is generally cylindrical or annular in shape and includes prosthetic leaflets coupled to the interior of a stent or frame. The leaflets are configured to transition from an open configuration, in which the leaflets are oriented in a direction substantially parallel to a longitudinal axis of the prosthetic valve, to a closed configuration, in which the leaflets are oriented substantially perpendicular to the longitudinal axis. In the open configuration, the leaflets permit a fluid to pass through the prosthetic valve in the flow direction, whereas in the closed configuration, the leaflets prevent the passage of fluid in a direction opposite the flow direction, thus preventing retrograde flow of the fluid.

An exemplary collapsible and/or expandable stent-supported prosthetic heart valve 100 which may incorporate various embodiments of the present disclosure is shown in FIG. 1. Valve 100 is shown in an expanded state, and includes a stent 110. Stent 110 may be formed from biocompatible materials that are capable of expansion, including, for example, shape memory alloys such as nitinol, or other suitable metals such as stainless steel, titanium, or other biocompatible metals. Stent 110 may alternatively be made of polyethylene or other hard or semi-hard polymers, and may be covered with a polyester velour to promote ingrowth. Stent 110 extends axially from an inflow end 112 to an outflow end 114. Stent 110 has an inflow section 113 adjacent inflow end 112, an outflow section 115 adjacent outflow end 114, and a transition section 116 extending between the inflow and outflow sections. Valve 100 tapers radially outward at transition section 116 from inflow section 113 to outflow section 115. As such, outflow section 115 has a larger diameter than inflow section 113. Each of the sections of stent 110 includes a plurality of struts 119 forming a plurality of cells 121 connected to one another in one or more annular rows around the stent. For example, as shown in FIG. 1, inflow section 113 may have two annular rows of complete cells 121 and outflow section 115 and transition section 116 may each have one or more annular rows of partial cells. Stent 110 may include one or more retaining elements 122 at outflow end 114, the retaining elements being sized and shaped to cooperate with female retaining structures (not shown) provided within a transcatheter delivery device. It should be noted that while the example of FIG. 1 is described as a prosthetic aortic valve having a stent with a shape as illustrated, the valve could be a bicuspid valve, such as the mitral valve, and the stent could have different shapes, such as a flared or conical inflow section, a less bulbous outflow section, and the like, and a differently shaped transition section between the inflow and outflow sections. Any details of the structure and function of the prosthetic heart valve 100 that are not described herein may be found in U.S. Pat. No. 10,143,551, the entire disclosure of which is hereby incorporated by reference herein.

Figure 3A:
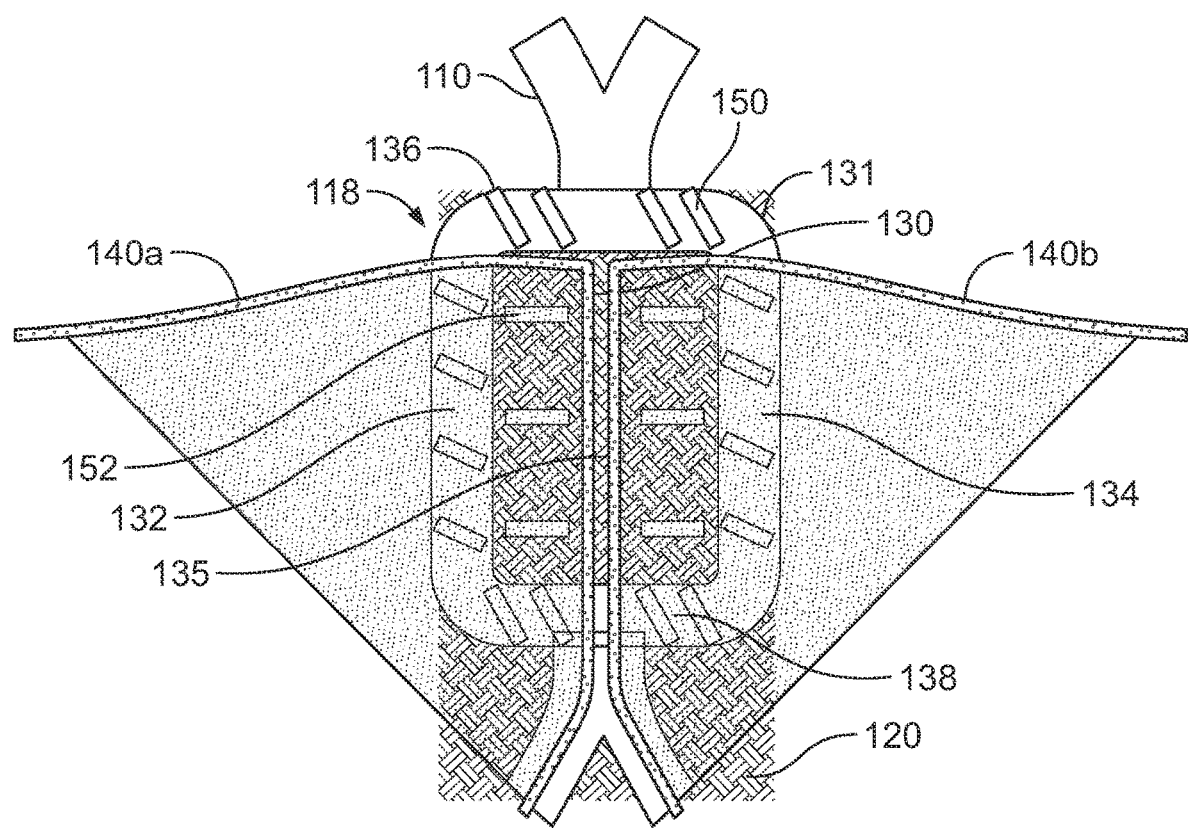
FIG. 3A is an enlarged schematic view of a commissure attachment feature and portions of the valve assembly of the heart valve of FIG. 1 in accordance with aspects of the disclosure.

Stent 110 includes one or more commissure attachment features 118, each of which may be disposed on inflow section 113 or at or near the junction between the inflow section and transition section 116. Each of commissure attachment features 118 includes an opening 130, which may be generally rectangular. A closer and more detailed view of one of commissure attachment features 118 is shown in FIG. 3A and described below in greater detail. Valve 100 further includes a valve assembly 117 including a skirt 120 coupled to the luminal surface of stent 110, to the abluminal surface of the stent, or to both the luminal and abluminal surfaces of the stent. Skirt 120 may be formed from a stretchable fabric. Valve assembly 117 further includes leaflets 140 that collectively function as a one-way valve by coapting with one another. As a prosthetic aortic valve, the prosthetic heart valve 100 has three leaflets 140. However, it will be appreciated that other prosthetic heart valves with which the leaflets of the present disclosure may be used may have a greater or lesser number of leaflets. Both the skirt 120 and leaflets 140 may be formed of any suitable biological material (e.g., animal tissue such as pericardium tissue), fabric, or polymer that is impermeable to liquid such as, for example, polytetrafluoroethylene (PTFE), polyvinyl alcohol (PVA), ultra-high molecular weight polyethylene (UHMWPE), silicone, urethane, and the like. Skirt 120 and leaflets 140 may be formed of the above materials or any of the additional materials described in co-pending U.S. provisional patent application 62/902,044, the disclosure of which is hereby incorporated by reference herein.

Leaflets 140 may be attached along their belly portions to cells 121 of stent 110, with the commissures between adjacent leaflets being attached to commissure attachment features 118. As can be seen in FIG. 1, each commissure attachment feature 118 may lie at the intersection of four cells 121, two of the cells being adjacent one another in the same annular row, and the other two cells being in different annular rows and lying in an end-to-end relationship. Each of the commissure attachment features 118 may include an opening 130 that facilitates the suturing of the leaflet commissure to stent 110. There are multiple approaches to addressing durability challenges at leaflet commissure attachment points. One approach is to design some compliance into the frame of the device. This allows stress to be shared between the leaflet and the frame and thus reduces the peak stress on a single component. This disclosure is directed to design features for improvement of commissure durability.

Figure 2:
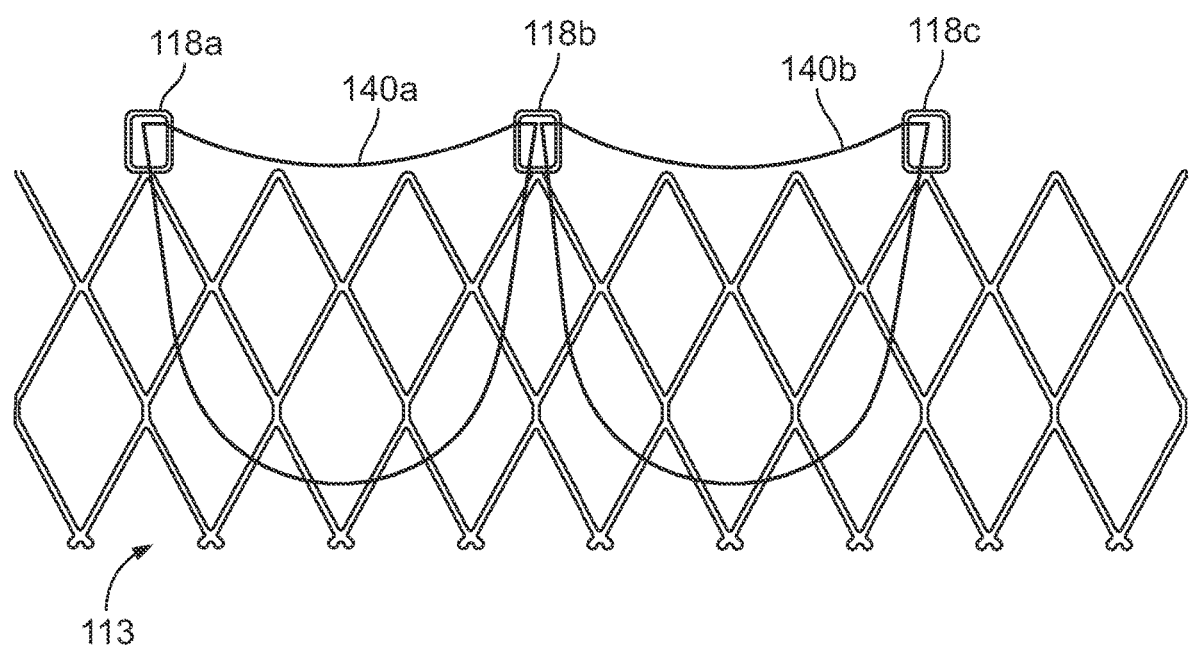
FIG. 2 is a schematic developed view of a portion of the heart valve of FIG. 1 in a flat, undeformed configuration.

Stent 110 may be formed from a milled or laser-cut tube of a shape-memory material such as nitinol. For example, FIG. 2 illustrates inflow section 113 of stent 110 as milled or laser-cut and unrolled into a flat sheet for ease of illustration. Inflow section 113 is shown with three commissure attachment features 118a, 118b, 118c, although a greater or lesser number of commissure features may be provided depending on the type of prosthetic heart valve and its number of leaflets. FIG. 2 shows two leaflets 140a, 140b coupled to commissure attachment features 118a, 118b, 118c, although for a prosthetic aortic valve there typically would be three such leaflets, with the third leaflet coupled between commissure attachment features 118c and 118a such that the leaflets collectively extend around the entire inner circumference of stent 110. Each leaflet extends from a first commissure attachment feature 118 to an adjacent commissure attachment feature. When valve 100 is in a final assembled configuration, each commissure attachment feature may have the commissure between a first end of a first leaflet and a second end of a second leaflet coupled thereto, such that each commissure attachment feature has two leaflets coupled thereto. For example, as shown in FIG. 2, first leaflet 140a is coupled to first commissure attachment feature 118a at a first end and to second commissure attachment feature 118b at a second end, and second leaflet 140b is coupled to the second commissure attachment feature at a first end and to third commissure attachment feature 118c at a second end.

FIG. 3A illustrates an enlarged view of commissure attachment feature 118 as shown from within the lumen of prosthetic heart valve 100. In the embodiment illustrated in FIG. 3A, commissure attachment feature 118 has a frame 131 defining opening 130. Frame 131 may have a substantially rectangular geometry formed by a first side portion 132, a second side portion 134, an upper portion 136 and a lower portion 138. Skirt 120 may be positioned on the luminal side of stent 110 (i.e., radially inward relative to the stent) and may be coupled to frame 131 using sutures 150. Alternatively, skirt 120 may be positioned on the abluminal side of stent 110 and may be coupled to frame 131 in a similar manner. Skirt 120 may be coupled to frame 131 with sixteen sutures 150. Sutures 150 may be positioned symmetrically around frame 131, with four sutures distributed evenly along first side portion 132, four sutures distributed evenly along second side portion 134, four sutures along upper portion 136 (two more proximate the first side portion and two more proximate the second side portion) and four sutures on lower side portion 138, which may or may not be aligned with the sutures on the upper portion. A number of sutures that is greater than or less than sixteen sutures may be used, and these may be distributed in any pattern around frame 131, such that the number of sutures on each portion of the frame may not be the same. Further illustrated in FIG. 3A, valve 100 includes leaflets 140a, 140b positioned internally of skirt 120 (i.e., radially inward relative to the skirt) and coupled to the skirt with sutures 152.

Figure 3B:
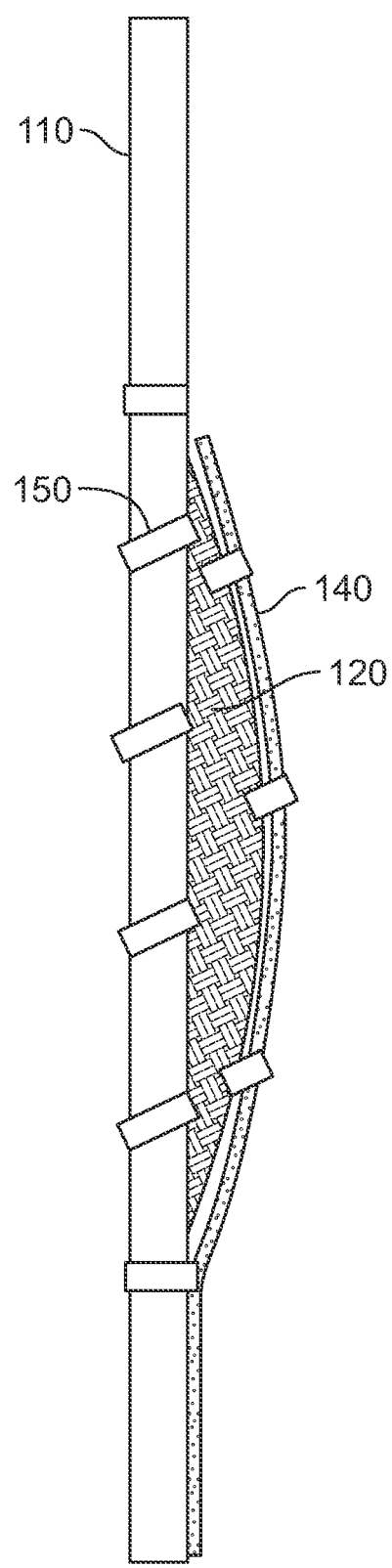
FIG. 3B is a schematic side view of the commissure attachment feature and portions of the valve assembly of FIG. 3A.

FIG. 3A shows first leaflet 140a and second leaflet 140b extending over a substantial portion of the height (i.e., the distance between upper portion 136 and lower portion 138) of opening 130, the leaflets being adjacent to and abutting one another at a center portion 135 of the opening. First leaflet 140a extends from center portion 135 in a first direction toward first side portion 132, and continues in the first direction over (radially inward of) and beyond the first side portion. Second leaflet 140b extends from center portion 135 in a second direction opposite the first direction toward second side portion 134, and continues in the second direction over (radially inward of) and beyond the second side portion. Leaflets 140a, 140b may be secured to stent 110 by the sutures 150 coupling skirt 120 to the side portions 132, 134 of frame 131. Additional sutures 152 may couple leaflets 140a, 140b to skirt 120 in opening 130. Sutures 152 may be evenly spaced and symmetrically positioned within opening 130. That is, three sutures 152 slightly offset from center portion 135 of opening 130 in the first direction may couple first leaflet 140a to skirt 120, and three sutures 152 slightly offset from the center portion of the opening in the second direction may couple second leaflet 140b to the skirt. It will be appreciated that more or less than a total of six sutures may be used to couple leaflets 140a, 140b to skirt 120 within opening 130. It is also contemplated that sutures 152 may be positioned at the commissure between leaflets 140 such that, for example, each suture couples first leaflet 140a to second leaflet 140b and both leaflets to skirt 120. FIG. 3B shows a side view of what is shown in FIG. 3A, in which skirt 120 is shown coupled to the side of stent 110 representing the interior of the stent. Leaflets 140 are shown coupled to skirt 120 on the side of the skirt opposite the stent side, representing the interior of the valve. Thus, skirt 120 is sandwiched between leaflets 140 and stent 110. As noted above, valve 100 may include three leaflets (the third leaflet not shown in FIG. 2) extending around the inner circumference of stent 110 in the fully assembled configuration, each leaflet being adjacent to the other two leaflets. Thus, prosthetic valve 100 may have three commissure attachment features 118 each having an opening 130, and each opening may have the skirt 120 and two leaflets 140 coupled thereto in the manner described above.

When valve 100 is implanted in a patient and operating as intended, leaflets 140 move between an open position and the closed position shown in FIG. 1 in which the leaflets occlude a central opening of valve assembly 117. Leaflets 140 are configured such that they are in the open position when blood pressure at inflow end 112 of stent 110 is greater than blood pressure at outflow end 114, and are in the closed position when blood pressure at the outflow end is greater than the blood pressure at the inflow end. In the open position, leaflets 140 may permit blood flow in the first direction, and may close to restrict blood flow in a second direction opposite the first direction. When leaflets 140 close, the back pressure of blood flow applies a force to the leaflets, resulting in stress applied to the region in which the leaflets are anchored to the valve. Such stress causes leaflets 140 to pull radially inward and deflect skirt 120 inward as shown in FIG. 3B. In the above-described embodiment, suturing leaflets 140 to stent 110 and skirt 120 may distribute the stress across multiple components (e.g., the leaflets, the skirt, and the stent), which may absorb the shock and dampen the high stresses that occur during leaflet closure.

In alternate embodiments, it is contemplated that the commissure attachment features of the stent may include a frame and an opening therein having any suitable geometry, such as triangular, diamond-shaped, or the like. For example, a diamond-shaped frame may define a single diamond-shaped opening such that the frame includes a first upper side portion, a second upper side portion, a first lower side portion and a second lower side portion. The skirt may be sutured to each side portion of the frame in a manner similar to that described above with reference to the rectangular frame. Alternatively, the skirt may be sutured to only some portions of the diamond-shaped frame and not others. That is, the skirt may be sutured to only the first upper side portion and the second lower side portion, or only the second upper side portion and the first lower side portion. Further, each of the leaflets may be sutured to the frame. For example, the first leaflet may be sutured to the first upper side portion and/or the first lower side portion, and the second leaflet may be sutured to the second upper side portion and/or the second lower side portion. In still further examples, a triangular shaped frame may define a single triangular opening such that the frame includes a first upper side portion, a second upper side portion and a lower portion. The skirt may be sutured to any or all of the frame portions, such as each of the first upper side portion, second upper side portion and lower portion.

In further examples, the commissure attachment features may be disposed anywhere on the valve, including the transition section or the outflow section. In other examples, the valve may include any number of leaflets suitable for promoting unidirectional flow and any number of commissure attachment features, preferably one commissure attachment feature for each leaflet such that each leaflet may couple to two commissure attachment features. In such examples, a valve having two leaflets may include two commissure attachment features, each having a frame and an opening therein as described above, and a valve having four leaflets may include four commissure attachment features, each having a frame and an opening therein as described above, etc. It is also contemplated that the skirt may have a first layer sutured to the interior of the stent and a second layer sutured to the exterior of the stent, and the leaflets may be sutured to at least one of the two layers of the skirt. The leaflets may be sutured to both the skirt and the stent for added anchoring strength and durability.

Figure 4A:
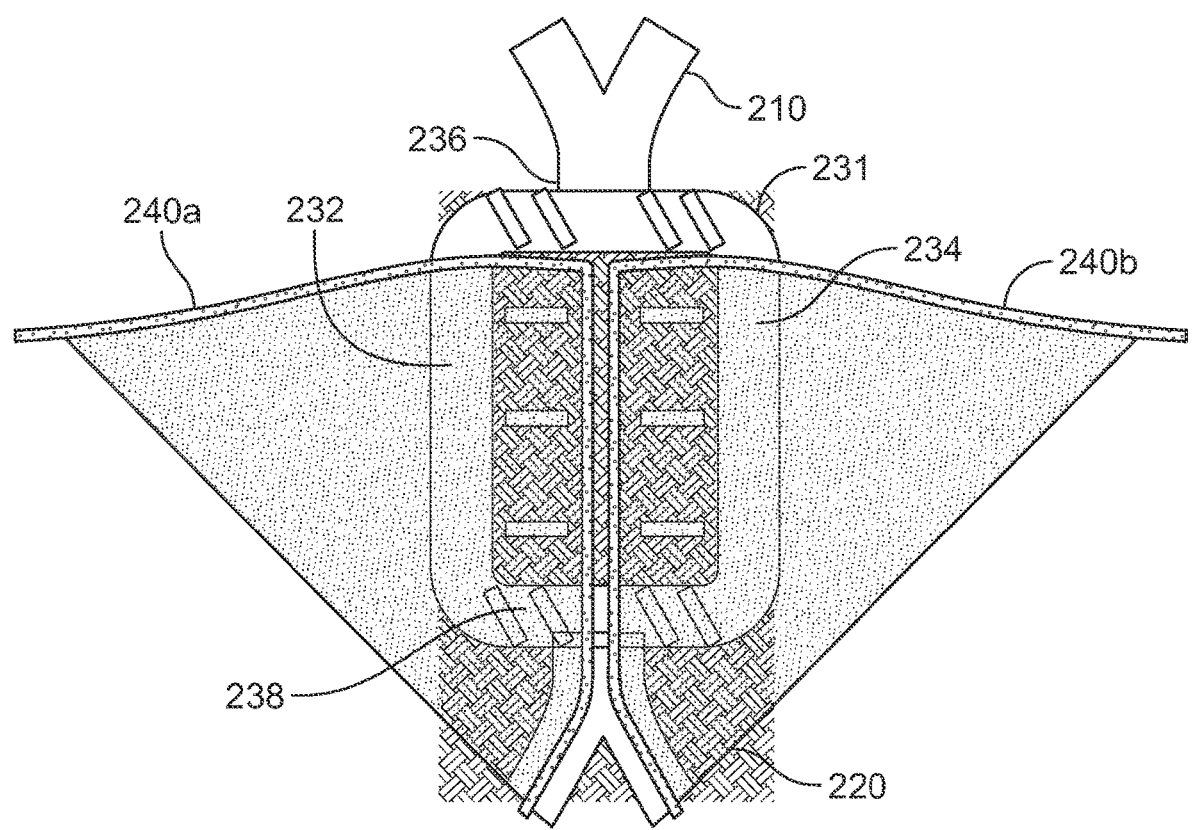
FIG. 4A is an enlarged schematic view of a commissure attachment feature and portions of the valve assembly of the heart valve of FIG. 1 in accordance with aspects of the disclosure.
Figure 4B:
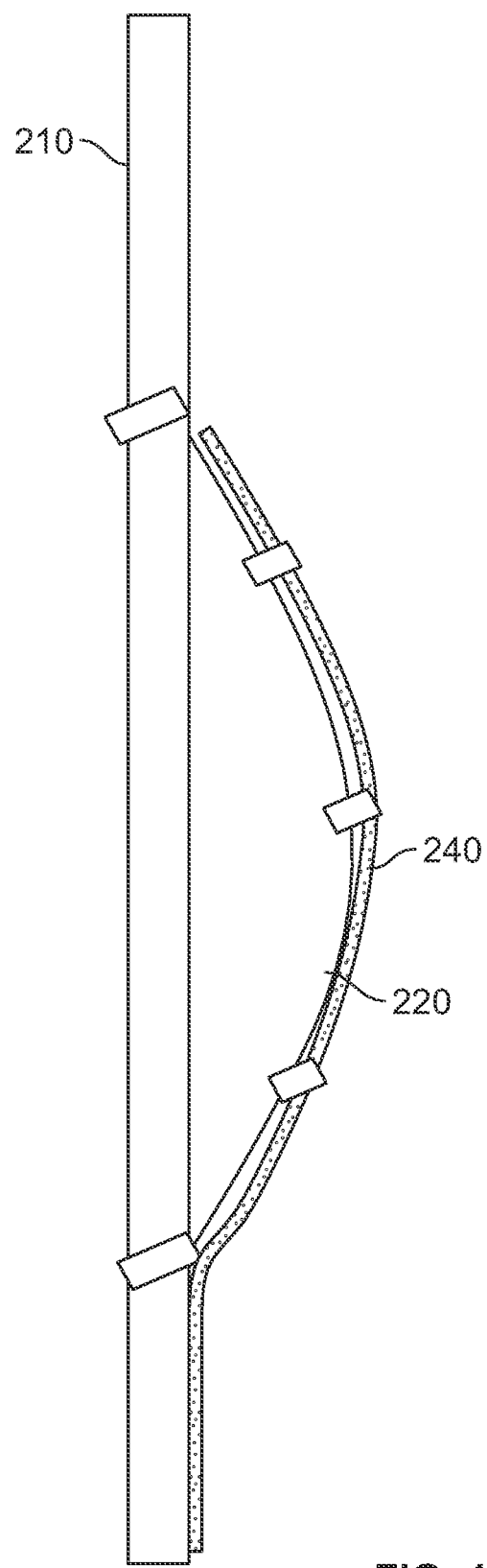
FIG. 4B is a schematic side view of the commissure attachment feature and portions of the valve assembly of FIG. 4A.

It is further contemplated that any number of sutures may be used to secure the skirt to the frame of the commissure attachment feature, and the sutures may be positioned in any suitable arrangement. For example, FIGS. 4A-B illustrate an alternate embodiment substantially similar to the embodiment shown in FIGS. 3A-B. Unless otherwise stated, like reference numerals refer to like elements of the above-described valve 100, but use the 200-series of numbers. Skirt 220 is sutured to stent 210 at upper portion 236 and lower portion 238 of frame 231, similar to skirt 120, but is not sutured to the first side portion 232 and second side portion 234 of the frame. Leaflets 240a, 240b are sutured to skirt 220 in the manner described above with reference to leaflets 140a, 140b and skirt 120 in FIG. 3A. When stress is applied to leaflets 240a, 240b, e.g., during closure of the valve, the leaflets may be pulled radially inward and deflect skirt 220 further inward relative to the deflection of skirt 120, forming a bump-out portion between upper portion 236 and lower portion 238 as illustrated in FIG. 4B. Such a configuration may distribute the forces acting on the valve to a greater extent among the leaflets, the skirt and the stent, resulting in a greater overall reduction of stresses within the valve during leaflet closure.

To summarize the foregoing, the present disclosure describes a prosthetic heart valve, including a stent extending from an inflow end to an outflow end, the stent having a commissure attachment feature between the inflow end and the outflow end, the commissure attachment feature having a frame defining an opening; a skirt coupled to the frame of the commissure attachment feature; and at least two leaflets coupled to the skirt, wherein each leaflet is coupled to the skirt both through the opening of the commissure attachment feature and outside of the commissure attachment feature; and/or the frame of the commissure attachment feature may be substantially rectangular; and/or the opening may be substantially rectangular and the frame may have a first side portion, a second side portion, an upper portion and a lower portion; and/or the skirt may be sutured to the first side portion, the second side portion, the upper portion and the lower portion; and/or the skirt may be sutured to only the upper portion and the lower portion of the frame; and/or the skirt may be configured to deflect radially inward from the frame of the commissure attachment feature, the skirt forming a bump-out portion between the upper portion and the lower portion; and/or a first one of the leaflets may be sutured to the first side portion; and/or a second one of the leaflets may be sutured to the second side portion; and/or the frame of the commissure attachment feature may be substantially diamond-shaped; and/or the opening of the commissure attachment feature may be a single diamond-shaped opening and the frame may have a first upper side portion, a second upper side portion, a first lower side portion and a second lower side portion; and/or the skirt may be sutured to the first upper side portion, the second upper side portion, the first lower side portion and the second lower side portion; and/or the skirt may be sutured to only the first upper side portion and the second lower side portion of the frame; and/or the skirt may be sutured to only the second upper side portion and the first lower side portion of the frame; and/or a first one of the leaflets may be sutured to the first upper side portion and the first lower side portion; and/or a second one of the leaflets may be sutured to the second upper side portion and the second lower side portion; and/or the skirt may include a first layer positioned radially inward of the stent and a second layer positioned radially outward of the stent, and the leaflets are coupled to the first and second layers of the skirt within the opening of the commissure attachment feature; and/or the skirt may be composed of a stretchable fabric; and/or the two leaflets may abut at a center portion of the opening of the commissure attachment feature and a suture couples the leaflets to each other and the skirt; and/or the frame of the commissure attachment feature may be substantially triangular and the opening may be substantially triangular, the frame having a first upper side portion, a second upper side portion, and a lower portion; and/or the skirt may be sutured to the first upper side portion, the second upper side portion and the lower portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that any of the features described in connection with individual embodiments may be shared with others of the described embodiments

The invention claimed is:

1. A prosthetic heart valve, comprising:
   a stent extending from an inflow end to an outflow end, the stent having a commissure attachment feature between the inflow end and the outflow end, the commissure attachment feature having a frame defining an outer perimeter that includes a first side portion, a second side portion, an upper portion and a lower portion, the first side portion, the second side portion, the upper portion and the lower portion collectively defining a single central opening;
   a skirt coupled to the frame of the commissure attachment feature along only the upper portion and the lower portion of the outer perimeter of the single central opening via a first set of sutures; and
   at least two leaflets coupled to the skirt, wherein each leaflet is coupled to the skirt both through the central opening of the commissure attachment feature via a second set of sutures and outside of the commissure attachment feature.

2. The prosthetic heart valve of claim 1, wherein the frame of the commissure attachment feature is substantially rectangular.

3. The prosthetic heart valve of claim 1, wherein the skirt is sutured to the first side portion, the second side portion, the upper portion and the lower portion via the first set of sutures.

4. The prosthetic heart valve of claim 1, wherein the skirt is configured to deflect radially inward from the frame of the commissure attachment feature, the skirt forming a bump-out portion between the upper portion and the lower portion.

5. The prosthetic heart valve of claim 1, wherein a first one of the leaflets is sutured to the first side portion.

6. The prosthetic heart valve of claim 5, wherein a second one of the leaflets is sutured to the second side portion.

7. The prosthetic heart valve of claim 1, wherein the skirt includes a first layer positioned radially inward of the stent and a second layer positioned radially outward of the stent, and the leaflets are coupled to the first and second layers of the skirt within the central opening of the commissure attachment feature.

8. The prosthetic heart valve of claim 1, wherein the skirt is composed of a stretchable fabric.

9. The prosthetic heart valve of claim 1, wherein the two leaflets abut at a center portion of the central opening of the commissure attachment feature and the second set of sutures couples the leaflets to each other and the skirt.

* * * * *